United States Patent [19]

Hettiarachchi

[11] Patent Number: 5,600,692
[45] Date of Patent: Feb. 4, 1997

[54] METHOD FOR IMPROVING TENACITY AND LOADING OF PALLADIUM ON PALLADIUM-DOPED METAL SURFACES

[75] Inventor: Samson Hettiarachchi, Menlo Park, Calif.

[73] Assignee: General Electric Company, Schenectady, N.Y.

[21] Appl. No.: 400,075

[22] Filed: Mar. 7, 1995

Related U.S. Application Data

[63] Continuation-in-part of Ser. No. 209,572, Mar. 10, 1994, which is a continuation-in-part of Ser. No. 143,513, Oct. 29, 1993, and a continuation-in-part of Ser. No. 143,514, Oct. 29, 1993, Pat. No. 5,448,605.

[51] Int. Cl.$^6$ ............................................. G21C 9/00
[52] U.S. Cl. ..................... 376/305; 376/306; 422/11; 422/14; 422/19
[58] Field of Search ........................... 376/301, 305, 376/306, 356, 357; 422/11, 14, 19

[56] References Cited

U.S. PATENT DOCUMENTS

| | | | |
|---|---|---|---|
| 3,023,085 | 2/1962 | McBride | 423/580.1 |
| 3,250,683 | 5/1966 | Gustavson et al. | 376/323 |
| 3,523,824 | 8/1970 | Powers et al. | 427/131 |
| 3,531,538 | 9/1970 | Duerksen et al. | 260/674 |
| 3,816,344 | 6/1974 | Shimizu et al. | 252/455 R |
| 3,900,320 | 8/1975 | Rolker et al. | 430/324 |
| 4,004,055 | 1/1977 | Hess et al. | 427/431 |
| 4,093,559 | 6/1978 | Fernholz et al. | 252/443 |
| 4,376,753 | 3/1983 | Lucas | 376/305 |
| 4,842,811 | 6/1989 | Desilva | 376/301 |
| 4,940,564 | 7/1990 | Aizawa et al. | 376/306 |
| 5,035,875 | 7/1991 | Daish | 423/580 |
| 5,130,080 | 7/1992 | Niedrach | 376/305 |
| 5,130,081 | 7/1992 | Niedrach | 376/305 |
| 5,135,709 | 8/1992 | Andresen et al. | 376/305 |
| 5,164,152 | 11/1992 | Kim et al. | 376/305 |
| 5,292,361 | 3/1994 | Otsuka et al. | 106/1.28 |

FOREIGN PATENT DOCUMENTS

| | | |
|---|---|---|
| 0450444A1 | 10/1981 | European Pat. Off. . |
| 0140587 | 5/1985 | European Pat. Off. . |
| 0265723 | 5/1988 | European Pat. Off. . |
| 0450440A1 | 10/1991 | European Pat. Off. . |
| 0526160 | 2/1993 | European Pat. Off. . |
| 0651073A1 | 5/1995 | European Pat. Off. . |
| 0651397A1 | 5/1995 | European Pat. Off. . |
| 0671486A1 | 9/1995 | European Pat. Off. . |
| 9218665 | 10/1992 | WIPO . |

OTHER PUBLICATIONS

Derwent Publications Ltd., London, GB; AN 84–059353 & JP–A–59 016 983 (Katayama Kagaku Kogyo Kenkyush), Abstract.

*Primary Examiner*—Charles T. Jordan
*Assistant Examiner*—Chrisman D. Carroll
*Attorney, Agent, or Firm*—Nixon & Vanderhye

[57] ABSTRACT

A method for mitigating crack growth on the surface of stainless steel or other alloy components in a water-cooled nuclear reactor wherein a solution or suspension of a compound containing a noble metal is injected into the coolant water along with a reducing agent. The presence of the reducing agent will assist in better deposition of the noble metal, for example, palladium, on metal surfaces, thereby increasing the noble metal loading and also improving the tenacity with which the noble metal is bound onto the metal. The extent of noble metal doping is important in providing a better (lower) ECP response of the metal in the presence of a stoichiometric ratio of $H_2$ to $O_2$, which reduces the hydrogen demand considerably. The more tenacious the noble metal is bound to the metal surface, the longer its expected life will be, particularly under in-reactor Situations where the metal surfaces are subjected to a variety of hydrodynamic conditions.

19 Claims, 2 Drawing Sheets

METHOD FOR IMPROVING TENACITY AND LOADING OF PALLADIUM ON PALLADIUM-DOPED METAL SURFACES

RELATED PATENT APPLICATIONS

This application is a continuation-in-part application of U.S. patent application Ser. No. 08/209,572, filed on Mar. 10, 1994, which in turn is a continuation-in-part application of U.S. patent application Ser. No. 08/143,513 and U.S. Ser. No. 08/143,514, now U.S. Pat. No. 5,448,605, both filed on Oct. 29, 1993.

FIELD OF THE INVENTION

This invention relates to reducing the corrosion potential of components exposed to high-temperature water. As used herein, the term "high-temperature water" means water having a temperature of about 150° C. or greater or steam. High-temperature water can be found in a variety of known apparatus, such as water deaerators, nuclear reactors, and steam-driven power plants.

BACKGROUND OF THE INVENTION

Nuclear reactors are used in electric power generation, research and propulsion. A reactor pressure vessel contains the reactor coolant, i.e. water, which removes heat from the nuclear core. Respective piping circuits carry the heated water or steam to the steam generators or turbines and carry circulated water or feedwater back to the vessel. Operating pressures and temperatures for the reactor pressure vessel are about 7 MPa and 288° C. for a boiling water reactor (BWR), and about 15 MPa and 320° C. for a pressurized water reactor (PWR). The materials used in both BWRs and PWRs must withstand various loading, environmental and radiation conditions.

Some of the materials exposed to high-temperature water include carbon steel, alloy steel, stainless steel, and nickel-based, cobalt-based and zirconium-based alloys. Despite careful selection and treatment of these materials for use in water reactors, corrosion occurs on the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners and welds, exposed to high-temperature water. As used herein, SCC refers to cracking propagated by static or dynamic tensile stressing in combination with a corrosive environment. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, crevice geometry, heat treatment, and radiation can increase the susceptibility of metal in a component to SCC.

It is well known that SCC occurs at higher rates when oxygen is present in the reactor water in concentrations of about 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the kinetic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote intergranular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding dissolved hydrogen to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in high-temperature water to below a critical potential required for protection from IGSCC. As used herein, the term "critical potential" means a corrosion potential at or below a range of values of about −230 to −300 mV based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen increases the ECP of metals exposed to the water above the critical potential, whereas water with little or no oxidizing species present results in an ECP below the critical potential.

It has been shown that IGSCC of Type 304 stainless steel (containing 18–20% Cr, 8–10.5% Ni and 2% Mn) used in BWRs can be mitigated by reducing the ECP of the stainless steel to values below −230 mV(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five to eight. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

An effective approach to achieve this goal is to either coat or alloy the alloy surface with noble metal. The term "noble metal" as used herein encompasses palladium, platinum, ruthenium, rhodium, osmium, iridium and mixtures thereof. Palladium doping has been shown to be effective in mitigating the crack growth rate in Type 304 stainless steel, Alloy 182 and Alloy 600. The techniques used to date for palladium coating include electroplating, electroless plating, hyper-velocity oxy-fuel, plasma deposition and related high-vacuum techniques. Palladium alloying has been carried out using standard alloy preparation techniques. These approaches are ex situ techniques in that they cannot be practiced while the reactor is in operation. Also noble metal coatings such as those applied by plasma spraying and by hyper-velocity oxy-fuel must be applied to all surfaces that require protection, i.e., they afford no protection to adjacent uncoated regions.

One method of in situ application of a noble metal onto stainless steel or other metal surfaces inside a boiling water reactor is by injecting a decomposable noble metal compound into the high-temperature (i.e., 550° F.) water that is in contact with the metal surface during reactor operation. As a result of decomposition of the noble metal compound, the oxide film on the metal surfaces becomes doped with noble metal. The amount of noble metal dopant can be made high enough to provide sufficient catalytic activity for $H_2$ and $O_2$ recombination to reduce the ECP of the metal surfaces to required protection values. This approach of noble metal doping has been shown to be effective against crack initiation and crack growth in stainless steel at $H_2/O_2$ molar ratios greater than 2 in the high-temperature reactor environment.

A previously disclosed in situ doping technique involved the injection of a thermally decomposable noble metal compound such as palladium acetylacetonate into the high-temperature water in contact with stainless steel surfaces. This method dopes the oxide film on the stainless steel surface with palladium and provides sufficient catalytic activity for $H_2$ and $O_2$ recombination that reduces the ECP of stainless steel surfaces to required protection values. Palladium doping has been accomplished even with palladium nitrate, indicating that the doping process works even with inorganic compounds. A similar doping was successfully performed with platinum using platinum acetylacetonate. Thus, doping of noble metal can be achieved by adding a noble metal compound into the high-temperature water. This approach of noble metal doping has been shown to be effective against crack initiation and crack growth of stainless steel, Alloy 182 and Alloy 600 at molar ratios of $H_2/O_2 > 2$.

SUMMARY OF THE INVENTION

The present invention is an improved method for the in situ application of palladium or other noble metal onto stainless steel or other metal surfaces inside a BWR. The method comprises the step of injecting into the high-temperature water of a BWR a solution or suspension of a compound containing a noble metal along with a reducing agent. The noble metal compound and the reducing agent can be injected as a mixture or as separate liquid streams. Alternatively, the reducing agent is injected first and then the noble metal compound and the reducing agent are injected simultaneously. As used in the claims set forth hereinafter, the term "solution" means solution or suspension.

The presence of the reducing agent will assist in better deposition of the noble metal, for example, palladium, on metal surfaces, thereby increasing the noble metal loading (>3 at .%) and also improving the tenacity with which the noble metal is bound onto the metal. The extent of noble metal doping is important in providing a better (lower) ECP response of the metal in the presence of a slight excess of hydrogen or a stoichiometric ratio of $H_2$ to $O_2$, which reduces the hydrogen demand considerably, thereby minimizing the negative side effects of $^{16}N$. The tenacious nature of the noble metal on the metal surface is important from a durability standpoint. The more tenacious the noble metal is bound to the metal surface, the longer its expected life will be, particularly under in-reactor situations where the metal surfaces are subjected to a variety of hydrodynamic conditions. Thus, improved long-term catalytic ECP response is expected from metal surfaces that have been exposed to the injection of a noble metal compound during and/or after the injection of a reducing agent in a high-temperature aqueous environment.

The passive oxide films on the surfaces of structural materials can be doped or coated with palladium or other noble metal using either in situ or ex situ techniques. In accordance with both techniques, the structural material is immersed in high-temperature water containing a noble metal compound and a reducing agent. Noble metal ions or atoms are freed by thermal decomposition and more effectively reduced by the reducing agent. As used in the claims set forth hereinafter, the term "species" means ions or atoms. The reduced noble metal then binds to the oxide film or crud on the alloy surfaces with increased loading and improved tenacity. Thus, the presence of a reducing agent during noble metal doping increases the duration of the effects of noble metal doping, i.e., mitigation of crack growth and prevention of crack initiation.

DETAILED DESCRIPTION OF THE PREFERRED EMBODIMENTS

Figure 1:
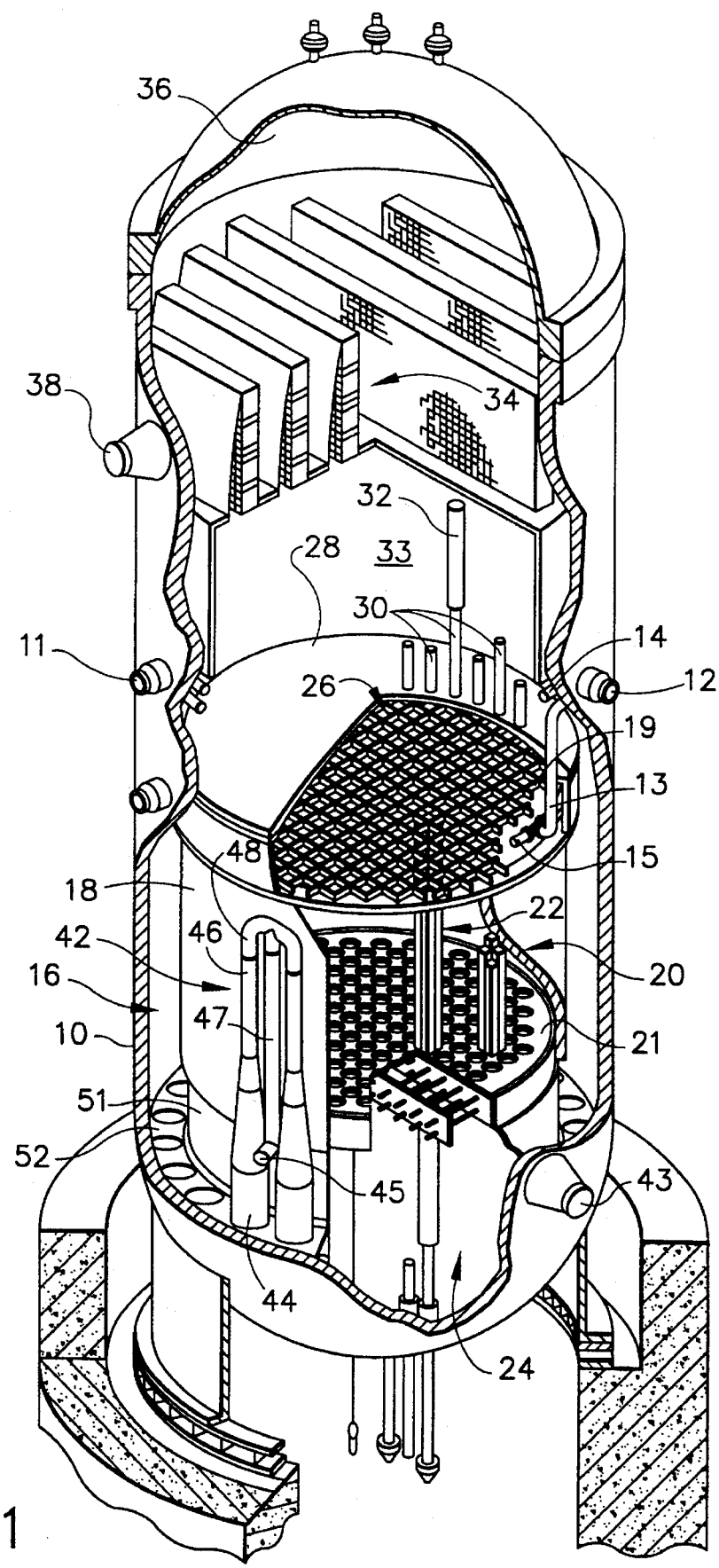
FIG. 1 is a schematic showing a partially cutaway perspective view of a conventional BWR.

The fluid flow in a boiling water reactor will be generally described with reference to FIG. 1. Feedwater is admitted into a reactor pressure vessel (RPV) 10 via a feedwater inlet 12 and a feedwater sparger 14, which is a ring-shaped pipe having suitable apertures for circumferentially distributing the feedwater inside the RPV. A core spray inlet 11 supplies water to a core spray sparger 15 via core spray line 13. The feedwater from feedwater sparger 14 flows downwardly through the downcomer annulus 16, which is an annular region between RPV 10 and core shroud 18. Core shroud 18 is a stainless steel cylinder which surrounds the core 20 comprising numerous fuel assemblies 22 (only two 2×2 arrays of which are depicted in FIG. 1). Each fuel assembly is supported at the top by top guide 19 and at the bottom by core plate 21. Water flowing through downcomer annulus 16 then flows to the core lower plenum 24.

The water subsequently enters the fuel assemblies 22 disposed within core 20, wherein a boiling boundary layer (not shown) is established. A mixture of water and steam enters core upper plenum 26 under shroud head 28. Core upper plenum 26 provides standoff between the steam-water mixture exiting core 20 and entering vertical standpipes 30, which are disposed atop shroud head 28 and in fluid communication with core upper plenum 26.

The steam-water mixture flows through standpipes 30 and enters steam separators 32, which are of the axial-flow centrifugal type. The separated liquid water then mixes with feedwater in the mixing plenum 33, which mixture then returns to the core via the downcomer annulus. The steam passes through steam dryers 34 and enters steam dome 36. The steam is withdrawn from the RPV via steam outlet 38. the core necessary to attain the required power density. The BWR also includes a coolant recirculation system which provides the forced convection flow through. A portion of the water is sucked from the lower end of the downcomer annulus 16 via recirculation water outlet. 43 and forced by a centrifugal recirculation pump (not shown) into jet pump assemblies 42 (only one of which is shown) via recirculation water inlets 45. The BWR has two recirculation pumps, each of which provides the driving flow for a plurality of jet pump assemblies. The pressurized driving water is supplied to each jet pump nozzle 44 via an inlet riser 47, an elbow 48 and an inlet mixer 46 in flow sequence. A typical BWR has 16 to 24 inlet mixers.

The present invention is a technique for coating or doping the oxide film or crud formed on metal surfaces of reactor components with noble metal having increased loading and improved tenacity. In accordance with the preferred technique, the noble metal is brought into contact with the oxide layer by injecting a noble metal-containing compound into the coolant water during reactor operation. Preferably the noble metal compound is injected at a point upstream of the feedwater inlet or into the recirculation water. At the same time, a reducing agent is injected into the coolant water. The noble metal compound and the reducing agent can be injected as a mixture or as separate liquid streams. Alternatively, the reducing agent is injected first and then the noble metal compound and the reducing agent are injected simultaneously.

Suitable reducing agents include sodium borohydride, sodium hypophosphite, hydrazine, formaldehyde and stannous salts, e.g., stannous acetate. However, other reducing agents may provide a similar benefit when added to the coolant water during noble metal compound injection.

In accordance with the prior technique, a noble metal compound is injected into the high-temperature water of a BWR. The high temperatures as well as the gamma and neutron radiation in the reactor core act to decompose the compound, thereby freeing Pd ions or atoms for deposition on the oxide film surfaces. One Pd-containing compound successfully used for this purpose is an organometallic compound, palladium acetylacetonate. However, other palladium compounds of organic, organometallic and inorganic nature have also been used for this purpose.

Tests have shown that after palladium treatment, crack growth in stainless steel is mitigated even in the presence of substoichiometric levels of hydrogen. The ECP value of the stainless steel surfaces inside the crack remain quite negative and below the required IGSCC critical potential of $-0.230$ V(SHE) even under conditions where the ECP value of stainless steel surfaces outside the crack is above the critical potential.

Experiments were performed to determine the ECP response of Pd-doped Type 304 stainless steel by injecting an organometallic palladium compound, i.e., palladium acetylacetonate, into an autoclave that formed part of a high-temperature recirculating flow loop. The autoclave had a constant extension rate tensile (CERT) specimen made of Type 304 stainless steel and a stainless steel tip electrode also made of Type 304 stainless steel. The reference electrodes used to measure ECPs consisted of a $Cu/Cu_2O/ZrO_2$ type reference electrode and an external pressure balanced Ag/AgCl, 0.1M KCl reference electrode. The recirculating flow loop contained deionized water heated to 550° F. inside the autoclave. The oxygen level in the effluent water was 200 ppb.

The palladium acetylacetonate injection solution was prepared by dissolving 52.6 mg of palladium acetylacetonate powder in 40 ml of ethanol. The ethanol solution is then diluted with water. After dilution, 10 ml of ethanol are added to the solution. This is then diluted to a volume of 1 liter. Alternatively, a water-based suspension can be formed, without using ethanol, by mixing palladium acetylacetonate powder in water.

Figure 2:
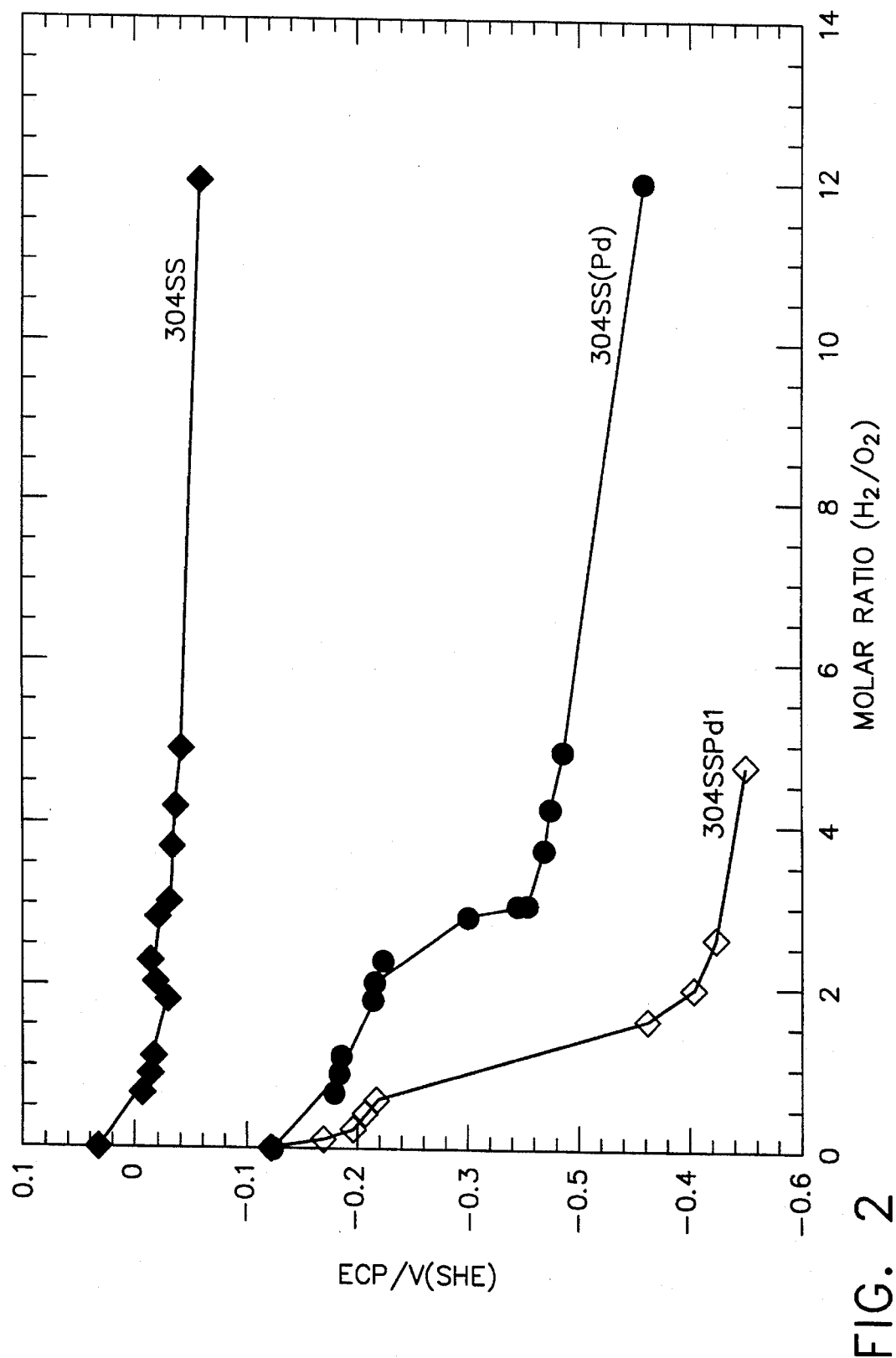
FIG. 2 is a plot showing the ECP response as a function of the molar ratio of hydrogen to oxygen for three Type 304 stainless steel specimens: 304SS—not doped with palladium; 304SS(Pd)—doped with 58 ppb Pd; and 304SSPd1—doped with 96 ppb Pd.

In one experiment, palladium acetylacetonate compound, dissolved in the ethanol/water mixture, was injected into the inlet side of the main pump in the flow loop using an injection pump at a rate so that the solution entering the autoclave (at 550° F.) had a Pd concentration of ~58 ppb. In another experiment, palladium acetylacetonate compound was injected at a rate so that the solution entering the autoclave had a Pd concentration of ~96 ppb. The results of these experiments are depicted in FIG. 2.

For the 58 ppb Pd-doped specimen, the ECP reaches a value of $-0.220$ V(SHE) at a $H_2/O_2$ molar ratio of 2, whereas at the same molar ratio the 96 ppb Pd-doped specimen shows an ECP of $-0.520$ V(SHE). The latter specimen almost behaved like a pure platinum or pure palladium specimen. Thus, palladium doping of Type 304 stainless steel can achieve the IGSCC protection potential at a $H_2/O_2$ molar ratio of 2–2.5. For the same molar ratios, the ECP of undoped Type 304 stainless steel was $-0.020$ V(SHE), which is considerably higher than the IGSCC protection potential of $-0.230$ V(SHE).

Experiments have demonstrated the effectiveness of palladium doping in crack mitigation in Alloy 182, Alloy 600 and Type 304 stainless steel. During palladium doping, palladium is deposited on the exposed surfaces of a metal specimen as well as inside the crack on interior surfaces thereof. The palladium is held on the surfaces by physical forces, such as physical adsorption or by chemical forces via an ion exchange displacement reaction where an iron, chromium or nickel atom is replaced by a noble metal atom. Thus, under low-flow conditions, palladium may remain on the surfaces of components as well as inside cracks, resulting in low ECPs under excess hydrogen. This situation mitigates cracking as long as palladium remains on the surfaces. However, under high-flow conditions it is possible that a portion of the surface palladium may be removed by the shear flow of the fluid. As a result, the catalytic activity of the surface may decrease.

In contrast, in accordance with the deposition technique of the present invention, the reducing agent supplies electrons to the palladium in a reaction that chemically binds the palladium atoms to the doped surface. During this reaction, the reducing agent supplies electrons that reduce the palladium to the zero valence state. This process is similar to electroless plating, except that the high temperatures inside the reactor make the use of aggressive chemicals, such as hydrofluoric acid or ammonium chloride, unnecessary. For example, if sodium hypophosphite is added during palladium compound injection, the following reaction occurs following decomposition of the compounds:

$$2H_2PO_2^- + 2H_2O + Pd^{2+} \rightarrow Pd^0 + H_2 + 4H^+ + 2HPO_3^{2-}$$

As a result of the presence of a reducing agent during injection of the decomposable noble metal compound, the loading and tenacity of the deposited noble metal are increased. Thus, the noble metal deposited on the exposed metal surfaces will be less susceptible to being removed by high shear fluid flow inside the reactor. The increased levels of noble metal on the metal sufaces provide enhanced crack mitigation even under high-shear flow conditions such as those experienced in a BWR.

It will be appreciated that, in theory, the technique of the present invention is not limited to in situ applications. Reactor components could be treated with noble metal at a treatment facility outside the reactor as long as the treatment temperature and pressure are sufficiently high. For example, stainless steel components could be immersed in a pressure vessel filled with high-temperature water having a noble metal compound and a reducing agent added thereto. Alternatively, the surface may be exposed to the reducing agent prior to simultaneous injection of the noble metal and reducing agent. After exposing the metal surfaces to the reduced noble metal in solution for the time required to achieve protection levels of noble metal doping, the protected components can then be installed inside a reactor.

The foregoing method has been disclosed for the purpose of illustration. Variations and modifications of the disclosed method will be readily apparent to practitioners skilled in the art of reactor kinetics. For example, noble metals other than palladium or mixtures of noble metals can be applied using this technique. A noble metal can be injected in the form of an organic, inorganic or organometallic compound to reduce the potential of reactor components made of stainless steel or other alloys. All such variations and modifications are intended to be encompassed by the claims set forth hereinafter.

I claim:

1. A method for mitigating initiation or propagation of a crack in an oxided metal component immersed in water, comprising the steps of:

injecting a solution of a compound containing a noble metal into the water, said noble metal having the property of decreasing the electrochemical potential of said oxided metal component;

causing said compound to decompose in high-temperature water to release species of said noble metal which incorporate in said oxided metal component surface;

adding a reducing agent to the water to reduce the noble metal freed by decomposition of the noble metal compound.

2. The method as defined in claim 1, wherein said metal component is made of an alloy selected from the group consisting of stainless steel, nickel-based alloy and nickel-chromium-iron alloy.

3. The method as defined in claim 1, wherein said noble metal is palladium.

4. The method as defined in claim 1, wherein said water is coolant water inside a nuclear reactor.

5. The method as defined in claim 1, wherein said reducing agent includes sodium borohydride.

6. The method as defined in claim 1, wherein said reducing agent includes sodium hypophosphite.

7. The method as defined in claim 1, wherein said reducing agent includes hydrazine.

8. The method as defined in claim 1, wherein said reducing agent includes formaldehyde.

9. The method as defined in claim 1, wherein said reducing agent includes a stannous salt.

10. A method of operating a boiling water reactor containing oxided metal components, comprising the steps of:

injecting a solution of a thermally decomposable compound containing a noble metal into the high-temperature water of an operating reactor to cause decomposition of said compound to produce species of said noble metal; and injecting a reducing agent into the high-temperature water to reduce the noble metal species freed by decomposition of the noble metal compound and to cause said noble metal species to incorporate in said oxided metal components, said injected reducing agent being present in the water during injection of the noble metal compound.

11. The method as defined in claim 10, wherein said noble metal compound includes palladium acetylacetonate.

12. The method as defined in claim 10, wherein said noble metal compound includes platinum acetylacetonate.

13. The method as defined in claim 10, wherein said noble metal compound includes palladium nitrate.

14. The method as defined in claim 10, wherein said reducing agent includes sodium borohydride.

15. The method as defined in claim 10, wherein said reducing agent includes sodium hypophosphite.

16. The method as defined in claim 10, wherein said reducing agent includes hydrazine.

17. The method as defined in claim 10, wherein said reducing agent includes formaldehyde.

18. The method as defined in claim 10, wherein said reducing agent includes a stannous salt.

19. A method of operating a boiling water reactor containing oxided metal components, comprising the steps of:

injecting a reducing agent into the high-temperature water during a first period of time;

simultaneously injecting a thermally decomposable compound containing a noble metal and more of said reducing agent into the high-temperature water during a second period of time to cause decomposition of said compound to produce noble metal species which incorporate in said oxided metal components, said reducing agent reducing said noble metal species freed by decomposition of the noble metal compound.

* * * * *